United States Patent [19]
Anzeveno et al.

[11] Patent Number: 5,227,479
[45] Date of Patent: Jul. 13, 1993

[54] PROCESS FOR THE PREPARATION OF NOJIRIMYCIN AND RELATED COMPOUNDS

[75] Inventors: Peter B. Anzeveno, Zionsville; Laura J. Creemer, Indianapolis, both of Ind.

[73] Assignee: Merrell Dow Pharmaceuticals Inc., Cincinnati, Ohio

[21] Appl. No.: 610,690

[22] Filed: Nov. 14, 1990

Related U.S. Application Data

[63] Continuation-in-part of Ser. No. 453,647, Dec. 20, 1989, abandoned.

[51] Int. Cl.$^5$ .................. C07H 1/00; B01J 23/42; B01J 21/00; C07D 211/40
[52] U.S. Cl. ................... 536/18.7; 536/17.4; 536/17.9; 536/55.3; 536/54; 546/219; 502/339
[58] Field of Search .............. 536/1.1, 4.1, 17.2, 536/17.4, 17.9, 18.7; 546/219; 502/339

[56] References Cited

U.S. PATENT DOCUMENTS 4,634,765  1/1987  Liu .
4,908,439  3/1990  Anzeveno ..................... 536/17.4

FOREIGN PATENT DOCUMENTS 3628486  2/1988  Fed. Rep. of Germany .

OTHER PUBLICATIONS

Mattingly et al., *J. Org. Chem.* 1983, 48, 3556 3559.
Lindsay, et al., *Phenyl Azide* (Benzene, azido-), *Organic Syntheses Collective Volume 3*, pp. 710–711, 1955.
Tsuda et al., *Chemical and Pharmaceutical Bulletin*, vol. 37, No. 10, pp. 2673–2678, (1989).
Stasik et al., *C.R. Acad. Sci., Ser. 2, 1990*, 311(5), 521.
Inouye et al., *Tetrahedron*, 24, 2125 (1968).
Saeki et al., *Chem. Pharm. Bull.*, 16, 2477 (1968).
Kinast et al., *Angew. Chem. Int. Ed. Engl.*, 20, 805 (1981).
Bernotas et al., *Tetrahedron Letters*, 26, 1123 (1985).
Bashyal et al., *Tetrahedron*, 43, 415 (1987).
Tsuda et al., *Heterocycles*, 27, 63 (1988).
Rajanikanth et al., *Tetrahedron Letters*, 30, 755 (1989).
Fleet et al., *Tetrahedron Letters*, 31, 405 (1990).
Fleet et al., *Tetrahedron Letters*, 31, 409 (1990).
Anzeveno et al., *Tetrahedron Letters*, 31, 2085 (1990).
Reitz et al., *Tetrahedron Letters*, 31, 6777 (1990).
Morrison and Boyd, "Organic Chemistry" 3rd Edition, published 1982 by Allyn and Bacon, Inc. (Boston), see p. 640.

*Primary Examiner*—Johnnie R. Brown
*Assistant Examiner*—Everett White
*Attorney, Agent, or Firm*—John J. Kolano

[57] ABSTRACT

The present invention relates to an efficient new route for the preparation of (+)-nojirimycin and (+)-1-deoxynojirimycin which involves the stereoselective reductive amination of 1,2-O-isopropylidene-5-oxo-α-D-glucuronolactone. The reductive amination uses particular oximes of the 5-oxo compound.

12 Claims, No Drawings

PROCESS FOR THE PREPARATION OF NOJIRIMYCIN AND RELATED COMPOUNDS

The present application is a continuation-in-part of U.S. application Ser. No. 453,647, filed Dec. 20, 1989, now abandoned.

BACKGROUND OF THE INVENTION

Homonojirimycin glycosides have been described in U.S. Pat. No. 4,634,765 as inhibitors of carbohydrate digestive enzymes and as antidiabetic compounds. The indicated compounds are prepared by the reaction of a protected glycosyl halide with an appropriately protected homonojirimycin compound. In the process described in the patent, the protected homonojirimycin compound is obtained by a cumbersome multi-step synthesis starting with the tetrabenzyl ether of D-glucopyranose. Thus, while the products in the patent would be available by the procedure described there, a method that would avoid the cumbersome synthesis would be attractive. Homonojirimycin itself was not used as an intermediate in the preparation of the protected homonojirimycin compound in U.S. Pat. No. 4,634,765 but it could be used in the overall synthesis if there was a procedure which would give the compound conveniently from available and inexpensive starting materials. Actually, such a procedure would have further value if it could also be used for the preparation of nojirimycin (a known glucosidase inhibitor) and desoxynojirimycin, with these indicated additional compounds obtained either specifically as intermediates or by appropriate modification of the procedure at some point.

One attractive and available starting material for the synthesis of compounds of the type discussed above would be D-glucuronolactone and reports have appeared in the literature on the use of this material in stereospecific syntheses of polyhydroxylated cyclic amino acids and also the conversion of such an amino acid to desoxynojirimycin. Specifically, Bashyal et al., *Tetrahedron*, 43, 415 (1987) describes procedures whereby D-glucuronolactone is reacted with acetone to give the acetonide and then the free C-5 OH is converted to the corresponding azide. By proper choice of reactions, it is possible to obtain either of the stereoisomeric azides. Bashyal then describes the catalytic reduction of the azide to the corresponding amine with the reaction mixture being treating immediately with benzyl chloroformate so that the amine product of the reduction is actually isolated as the corresponding carbamate. The acetonide group is then cleaved with acid to give the corresponding dihydroxy compound which is then hydrogenated in acetic acid to give, by a series of reactions, a trihydroxypipecolic acid. Bashyal also describes the hydrolysis of the azido acetonide to remove the acetonide and give the corresponding dihydroxy compound, followed by catalytic hydrogenation in acetic acid to also give a trihydroxypipecolic acid.

Bayer German OLS 36 28 486 also includes a similar conversion of an azido acetonide to a trihydroxypipecolic acid and, while the Bayer procedure appears to consist of more individual reaction steps, there was no effort to isolate any compound until the final pipecolic acid was obtained. It is noted that Bayer also includes a description of the reduction of this acid with sodium borohydride and boron trifluoride to give desoxynojirimycin. While this procedure and Bashyal can be used to obtain the compounds indicated, a disadvantage of both processes is the fact that they make use of azide intermediates and it would be preferable to avoid such compounds.

The synthesis of nojirimycin itself by an entirely different procedure using 5-amino-5-deoxy-1,2-O-isopropylidene-α-D-glucofuranose as an intermediate has been reported by Tsuda et al., *Heterocycles*, 27, 63 (1988). In that procedure, commercially available 1,2-isopropylidene-D-glucofuranose was used as the starting material. The regioselective oxidation of the C5-hydroxyl group in that compound gives the corresponding ketone which is then converted to the O-methyloxime. Reduction of the oxime then gives the amine referred to above. That amine is converted to nojirimycin via the bisulfite adduct by procedures which were previously reported. Although Tsuda indicates that his procedure would be a practical route to nojirimycin without chromatographic separation of the stereoisomers at any stage, nevertheless, it appears that chromatography is used to remove impurities and the conversion of the amine to nojirimycin actually gives a mixture of isomers and it is only because of the favorable crystallization of the nojirimycin bisulfite adduct that it is possible to obtain that material. In addition, although the second isomer remains in solution and does not affect the isolation of the nojirimycin adduct, the fact that it is formed in substantial amounts results in a reduction in the amount of nojirimycin that can be obtained.

SUMMARY OF THE INVENTION

The present invention thus relates to a new process for the synthesis of 1-deoxynojirimycin which could be modified to produce nojirimycin, homonojirimycin and related compounds and which avoids some of the disadvantages associated with the prior art processes. Specifically, the present invention relates to a new process for the preparation of 1-deoxynojirimycin starting from 1,2-O-ispropylidene-5-oxo-α-D-glucuronolactone hydrate. This process can be illustrated structurally as follows:

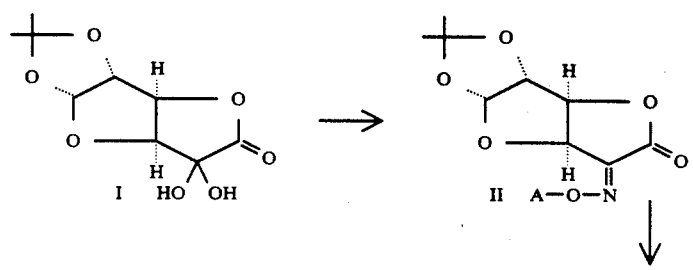

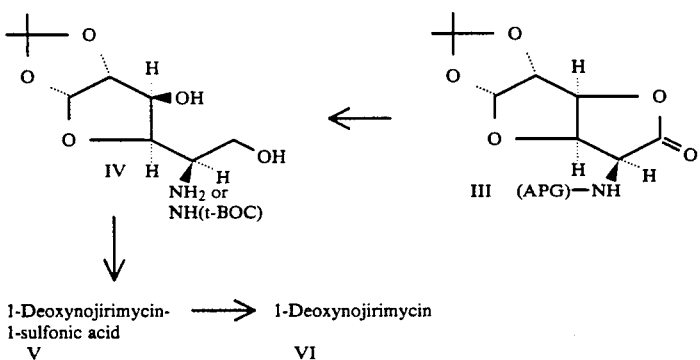

1-Deoxynojirimycin-  ⟶  1-Deoxynojirimycin
1-sulfonic acid
V                        VI In the structural formulas in the reaction scheme shown above, A is $C_{1-4}$ alkyl, benzyl or trimethylsilyl; APG is an amine protecting group; and t-BOC is t-butoxycarbonyl.

Specifically, the present invention relates to a process for converting 1,2-O-isopropylidene-5-oxo-α-D-glucuronolactone hydrate (I) to 1-deoxynojirimycin-1-sulfonic acid which comprises (a) reacting 1,2-O-isopropylidene-5-oxo-α-D-glucuronolactone hydrate with O-($C_{1-4}$ alkyl)hydroxylamine, O-benzylhydroxylamine or O-trimethylsilylhydroxylamine to give the corresponding oxime (II); (b) catalytically hydrogenating the oxime using palladium on carbon, in the presence of an amine protecting reagent to give 5-(APG)amino-5-deoxy-1,2-O-isopropylidene-α-D-glucuronolactone (III); (c) reducing the 5-(APG)-aminoglucuronolactone with a hydride reducing agent to give 5-amino-5-deoxy-1,2-O-isopropylidene-α-D-glucofuranose or, when APG is t-BOC, 5-(t-BOC)amino-5-deoxy-1,2-O-isopropylidene-α-D-glucofuranose (IV); and (d) reacting the glucofuranose with aqueous sulfur dioxide to give the desired 1-deoxynojirimycin-1-sulfonic acid.

The 1,2-O-isopropylidene-5-oxo-α-D-glucuronolactone hydrate (I) which serves as the starting material in the present process has been described in the literature where it has been prepared by the oxidation of 1,2-O-isopropylidene-α-D-glucuronolactone using manganese dioxide or other oxidizing agents. However, it has now been found that a Swern oxidation (oxalyl chloride, dimethylsulfoxide and triethylamine in methylene chloride at −70° C.) can be used or the oxidation can be carried out using calcium hypochlorite with ruthenium trichloride hydrate as a catalyst.

Compound I is then reacted with O-($C_{1-4}$ alkyl)hydroxylamine, O-benzylhydroxylamine or O-trimethylsilylhydroxylamine to give the corresponding O-substituted oxime of the 5-keto group (II). The O-methyl compound is preferred because the starting hydroxylamine is readily available and the oxime obtained is predominantly the E-isomer. However, the O-benzyl compound is also attractive because, in that case, only a single oxime isomer, the E-isomer, is obtained. It should be recognized that the general reference to the hydroxylamine reactants above is intended to encompass the use of those compounds in the form of the free base or their acid addition salts with strong inorganic acids, with the hydrochloride salts being preferred. The indicated preparation of the oximes is carried out using standard procedures for the preparation of such compounds. Although only three specific hydroxylamines/oximes have been referred to above, it should be recognized that other O-benzyl, O-trialkylsilyl or similar O-alkyl compounds would be considered as equivalent for the purposes of this invention.

The oxime (II) is then hydrogenated to the amine catalytically using palladium on carbon as the catalyst. The reduction takes place with high stereoselectivity to give the desired amine isomer. This hydrogenation can be carried out at a pressure of 1 to 3 atmospheres (98,000 to 294,000 Pa) and at a temperature from about room temperature to about 50° C. Preferred conditions for the hydrogenation are either 10% Pd on carbon or Pd(OH)$_2$ on carbon catalyst at 3 atmospheres (294,000 Pa) at room temperature in a solvent such as ethyl acetate. The reduction is carried out in the presence of an amine protecting reagent which will tie up the amine as soon as it is formed in the reaction mixture. This can be accomplished chemically using an anhydride such as t-BOC-anhydride which converts the amine to the corresponding t-BOC protected amine (III). Alternatively, the reaction can be carried out in the presence of anhydrous hydrogen chloride or an organic acid, such as trifluoroacetic acid, which would give the corresponding amine salt. In this case, the symbol APG used above would signify the acid itself together with the second hydrogen on the amine nitrogen. Use of protecting groups in this way avoids poisoning of the catalyst by the free amine and also avoids any undesired further reactions which might occur because of the presence of free amine.

The protected amine lactone (III) is then reduced using a hydride reducing agent in an inert solvent. This reduces the lactone to the corresponding N-protected diol (IV) when APG is BOC or, when the protecting group is a strong acid (salt), to the corresponding free amine diol. When APG is BOC, an equivalent amount of reducing agent is used and this serves to reduce the lactone selectively. When APG is an acid (salt), a large excess of hydride is used to reduce the acid and the lactone. Examples of hydride agents that can be used in this process are lithium aluminum hydride, sodium borohydride, lithium tri-t-butoxyaluminum hydride or diisobutylaluminum hydride. Lithium aluminum hydride is the preferred reducing agent for this reaction. Ethers are the preferred solvent for the reaction with tetrahydrofuran being particularly preferred. The reaction is generally carried out with cooling, preferably at about 0° C. When APG is an acid (salt), it is possible to combine the catalytic and the hydride reduction steps, without isolating the first reduction product, by simply filtering out the catalyst and proceeding with the hydride reduction.

Treatment of the N-protected diol (IV) with saturated aqueous sulfur dioxide at about 35°–40° C. serves to remove the isopropylidene protecting group and, when a t-BOC group is present, that group is also removed, and the resulting product first opens to an amino-aldehyde structure and recyclizes to give 1-deoxynojirimycin-1-sulfonic acid in good yield. Actually, it is also possible to remove the t-BOC group by treatment with base to give the corresponding free amine followed by treatment of that free amine with aqueous sulfur dioxide to give the sulfonic acid. The present process should also be considered as encompassing this two-step procedure.

The bisulfite adduct obtained above can be quantitatively converted to nojirimycin as described by Inouye et al., *Tetrahedron*, 24, 2125 (1968), and nojirimycin can be converted in 97% yield to deoxynojirimycin by the procedure described by Vasella et al., *Helv. Chim. Acta*, 65, 1134 (1982). In addition, nojirimycin can be converted to homonojirimycin by the procedure described by Anzeveno et al. in U.S. Pat. No. 4,880,917 which issued on Nov. 14, 1989.

The following examples are presented to illustrate the present invention.

DETAILED DESCRIPTION OF THE INVENTION

Example 1

1,2-O-Isopropylidene-5-oxo-α-D-glucuronolactone Hydrate (I)

To a cold (−70° C.) solution of dimethyl sulfoxide (10.7 g, 0.14 mol) in methylene chloride (200 mL) a solution of oxalyl chloride (8.0 mL, 0.09 mol) in methylene chloride (50 mL) was added dropwise at such a rate to maintain the reaction temperature below −55° C. After stirring for 0.5 hour below −70° C., a solution of 1,2-O-isopropylidene-α-D-glucuronolactone (10.0 g, 0.046 mol) in methylene chloride (100 mL) was added dropwise while again maintaining the reaction temperature below −55° C. The addition required 10 min After stirring at −70° C. for 3 h, triethylamine (18.0 mL, 0.13 mol) was added dropwise, again maintaining the temperature below −55° C. This addition required 5–10 min. After an additional 15 min, the cooling bath was removed, water (2.0 mL) added, and the reaction mixture allowed to warm to ambient temperature. Ethyl acetate (350 mL) was added and the resulting suspension poured through silica gel (250 mL) and eluted with ethyl acetate (500 mL). Concentration of the eluate left crude product (10.0 g, 94%). Recrystallization of a sample from ethyl acetate-hexane (1:1) gave pure 1,2-O-isopropylidene-5-oxo-α-D-glucuronolactone hydrate as colorless needles: mp 145°–148° C.; 1H NMR (acetone-d6) δ 1.41 (s, 3, $CH_3$), 1.57(s, 3, $CH_3$), 4.62 (d, 1, J=3.1 Hz, H-3), 4.91 (d, 1, J=3.7 Hz, H-2), 4.98 (d, 1, J=3.1 Hz, H-4), 5.26 (s, 1, OH), 5.50 (s, 1, OH), 6.03 (d, 1, J=3.7 Hz, H-1); mass spectrum, m/z (rel intensity) 215 ($M^+ + 1 - H_2O$, 100), 185 (15), 157 (12).

Example 2A 1,2-O-Isopropylidene-5-oxo-α-D-glucuronolactone O-Benzyloxime (II)

To a suspension of 1,2-O-isopropylidene-5-oxo-α-D-glucuronolactone hydrate (1.85 g, 7.9 mmol) in benzene (40 mL), O-benzylhydroxylamine hydrochloride (1.28 g, 7.9 mmol) was added and the resulting mixture refluxed for 3 hours. (Complete dissolution of the hydroxylamine and starting material occurred during this period.) The solution was then cooled and the solvent removed. Chromatographic purification of the residual viscous oil over silica gel (100 mL) with ethyl acetate-hexane (1:3) as eluent gave 2.51 g (99%) of 1,2-O-isopropylidene-5-oxo-α-D-glucuronolactone O-benzyloxime as a colorless viscous oil which slowly solidified on standing. NMR analysis showed a single oxime isomer present. An analytical sample was obtained as colorless prisms by recrystallization from benzene-hexane (1:1): mp 83°–85° C.; 1H NMR ($CDCl_3$) δ 1.36(s, 3, $CH_3$), 1.52 (s, 3, $CH_3$), 4.86 (d, 1, J=3.5 Hz, H-2), 4.91 (d, 1, J=4.4 Hz, H-3), 5.42 ('AB' subspectra, 2, $J_{AB}$=13.7 Hz, $CH_2$), 5.51 (d, 1, J=4.4 Hz, H-4), 6.00 (d, 1, J=3.5 Hz, H-1), 7.37 (m, 5, $C_6H_5$); 13C NMR ($CDCl_3$) δ 26.66, 27.34, 60.02, 72.22, 79.60, 83.15, 83.23, 107.07, 113.71, 128.54, 128.62, 128.74, 128.83, 135.46, 144.52, 162.96; mass spectrum, m/z (rel intensity) 320 ($M^+ + 1$, 100), 262 (15), 91 (90).

Example 2B 1,2-O-Isopropylidene-5-oxo-α-D-glucuronolactone O-(trimethylsilyl)oxime A well-stirred, nitrogen-blanketed mixture of 1,2-O-isopropylidene-5-oxo-α-D-glucuronolactone hydrate (0.45 g, 1.9 mmol) and O-(trimethylsilyl)hydroxylamine (0.24 g, 2.3 mmol) in benzene (30 mL) was heated to reflux, during which time a homogeneous solution was obtained, and refluxed for 2h. The reaction was cooled to ambient temperature and the solvent evaporated at reduced pressure. The residual thick oil was dissolved in ethyl acetate (~35 mL) and the solution filtered through a celite pad to remove any insoluble material. The filtrate was concentrated, leaving 0.6 g (~100%) of crude 1,2-O-isopropylidene-5-oxo-α-D-glucuronolactone O-(trimethylsilyl)oxime as an off-white, amorphous solid. This was an ~3:2 mixture of oxime stereoisomers by 1H NMR analysis, and was not further characterized. The crude oxime was used without further purification in subsequent reactions: 1H NMR (DMSO-d6) δ 6.03 (d, 1, J=4.0 Hz) 5.42 (d, 1, J=4.3 Hz) 5.05 (d, 1, J=4.3 Hz), 4.90 (d, 1, J=4.0 Hz), 1.44 (s, 1), 1.29 (s, 1), 0.00 (s, 9); mass spectrum (CI/$CH_4$) m/z (rel intensity) 302 ($M^+ + 1$, 4) 258 (12), 230 (100), 172 (40), 95 (60).

Example 2C 1,2-O-Isopropylidene-5-oxo-α-D-glucuronolactone O-Methyloxime

To a solution of 3.6 g (15.51 mmol) of 1,2-O-isopropylidene-5-oxo-α-D-glucuronolactone hydrate in pyridine (30 mL) was added 1.8 g (21.54 mmol) of O-methylhydroxylamine hydrochloride. The resulting solution was stirred at room temperature for 20 hours. The bulk of the pyridine was removed in vacuo (~2.0 mm) at ~40° C. The oily residue was dissolved in ethyl acetate (200 mL) and washed successively with water (20 mL), 1N HCl (2×20 mL), sat. $NaHCO_3$ (30 mL) and brine 20 mL) and dried ($MgSO_4$). Concentration left 3.8 9 of crude oxime which was purified by flash chromatography over silica gel (400 mL) using ethyl acetate hexane (1:3) as eluent. Pure 1,2-O-isopropylidene-5-oxo-α-D-glucuronolactone O-methyloxime (2.8 g, 74%) was obtained as a colorless oil, which solidified slowly on standing. This material by 1H NMR analysis was an approximate 96:4 mixture of E (major) and Z oxime isomers [from Integration of the two O-$CH_3$ resonances at δ 4.21 (E) and 4.18 (Z)]. Recrystallization of a sample from ethyl acetate hexane (1:4) gave pure E-oxime as colorless prisms, mp 73°–75° C.; $^1$H NMR (300 MHz, CDCl$_3$) δ 1.37 (s, 3), 1.54 (s, 3), 4.21 s, 3), 4.88 (d, 1, J=3.6 Hz, H2), 4.94 (d, 1, J=4.1 Hz, H3), 5.53 (d, 1, J=4.1 Hz, H4), 6.01 (d, 1, J=3.6 Hz, H1); mass spectrum, m/z (rel intensity) 244 (MH+, 100), 228 (25), 186 (65).

More careful chromatography of the 96:4 oxime mixture from 100× its weight in volume of silica gel using ethyl acetate-hexane (1:4) provided a sample of Z-oxime. This was recrystallized form ethyl acetate-hexane (1:3) to give pure material as colorless, jagged needles mp 136°–138° C.; $^1$H NMR (300 MHz, CDCl$_3$) δ 1.37 (s, 3), 1.53 (s, 3), 4.18 (s, 3), 4.87 (d, 1, J=3.7 Hz, H2), 4.92 (d, 1, J=3.9 Hz, H3), 5.24 (d, 1, J=3.9 Hz, H4), 6.03 (d, 1, J=3.7 Hz, H1); mass spectrum, m/z (rel intensity) 244 (MH+, 90), 212 (100), 186 (30).

Example 3A 5-(t-BOC)amino-5-deoxy-1,2-O-isopropylidene-α-D-glucuronolactone (III) from O-Benzyloxime To a solution of 1,2-O-isopropylidene-5-oxo-α-D-glucuronolactone O-benzyloxime (3.16 g, 9.9 mmol) and (t-BOC)$_2$O (2.38 g, 10.9 mmol) in ethyl acetate (20 mL) was added 0.5 g of 10% Pd/C and the resulting suspension stirred for 0.5 h under nitrogen. The catalyst was removed by filtration and washed with ethyl acetate (10 mL). Fresh Pd/C (0.9 g) was added to the filtrate, and the mixture hydrogenated on a Parr apparatus at 3 atmospheres for 60 h. The catalyst was filtered, washed with ethyl acetate (15 mL) and the filtrate concentrated. Chromatography of the residue over silica gel (80 mL) with ethyl acetate-hexane (1:3) as eluent yielded 1.85 g (59%) of 5-(t-BOC)amino-5-deoxy-1,2-O-isopropylidene-α-D-glucuronolactone. An analytical sample was obtained by recrystallization from ethyl acetate-hexane (1:1) as colorless needles: mp 157°–159° C.; $^1$H NMR (CDCl$_3$) δ 1.35 (s, 3, CH$_3$), 1.46 (s, 9, C$_4$H$_9$), 1.52 (s, 3, CH3), 4.78 (dd, 1, J=8.8, 4.2 Hz, H-5), 4.82 (d, 1, J=3.7 Hz, H-2), 4.84 (d, 1, J=3.0 Hz, H-3), 4.95 (dd, 1, J=4.2, 3.0 Hz, H-4), 5.10 (d, 1, J=8.8 Hz, NH), 5.93 (d, 1, J=3.7 Hz, H-1); mass spectrum, m/z(rel intensity) 316 (M+ +1, 5), 288 (20), 260 (100), 216 (40).

Example 3B 5-(t-BOC)amino-1,2-O-isopropylidene-α-D-glucuronolactone (III) from O-(trimethylsilyl)oxime When the procedure of Example 3A was repeated using 1,2-O-isopropylidene-5-oxo-α-D-glucuronolactone O-(trimethylsilyl)oxime in place of the O-benzyloxime, 5-(t-BOC)amino-5-deoxy-1,2-O-isopropylidene-α-D-glucuronolactone was obtained in an average yield of about 60%.

Example 3C 5-(t-BOC)amino-1,2-O-isopropylidene-α-D-glucuronolactone (III) from O-Methyloxime When the procedure of Example 3A was repeated using 1,2-O-isopropylidene-5-oxo-α-D-glucuronolactone O-Methyloxime in place of the O-benzyloxime, 5-(t-BOC)amino-5-deoxy-1,2-O-isopropylidene-α-D-glucuronolactone was obtained.

Example 4

5-(t-BOC)amino-5-deoxy-1,2-O-isopropylidene-α-D-glucofuranose (IV)

To a cold (−10° C.), well stirred suspension of lithium aluminum hydride (0.91 g, 23.9 mmol) and anhydrous tetrahydrofuran (15 mL), a solution of 5-(t-BOC-)amino-5-deoxy-1,2-O-isopropylidene-α-D-glucuronolactone (3.1 g, 9.8 mmol) in tetrahydrofuran (20 mL) was added dropwise during 40 min, maintaining a reaction temperature below 0° C. After stirring at 0° C. for 2 hours, the mixture was quenched while cold by the successive dropwise addition of water (1.0 mL), 1N sodium hydroxide solution (1.0 mL) and water (3.0 mL). This mixture was well stirred for 30 minutes at 0° C. and then filtered through a celite pad. The filter cake was washed with tetrahydrofuran (2×25 mL) and the combined filtrate and wash concentrated leaving 3.1 g of crude product. Flash chromatographic purification over silica gel (80 mL) using 8% acetone in methylene chloride as eluent afforded 2.8 g (90%) of pure 5-(t-BOC)amino-5-deoxy-1,2-O-isopropylidene-α-D-glucofuranose. An analytical sample was obtained as colorless needles by recrystallization from ethyl acetate-hexane (1:1). mp 115°–116° C.; 1H NMR (CDCl$_3$) δ 1.32 (s, 3, CH$_3$), 1.45 (s, 9, C$_4$H$_9$), 1.50 (s, 3, CH3), 1.97 (t, 1, J=6.3 Hz, OH), 3.7 (m, 2, H-5,6'), 4.06 (m, 3, H-3,4,6), 4.58 (d, 1, J=3.7 Hz, H-2), 4.99 (d, 1, J=2.4Hz, OH), 5.30 (d, 1, J=8.1 Hz, NH), 5.93 (d, 1, J=3.7 Hz, H-1); mass spectrum, m/z (rel intensity) 320 (M+ +1,40), 264 (60), 220 (100).

Example 4B

5-Amino-5-deoxy-1,2-O-isopropylidene-α-D-glucofuranose from 1,2-O-Isopropylidene-5-oxo-α-D-glucuronolactone O-Methyloxime A solution of 1,2-O-isopropylidene-5-oxo-α-D-glucuronolactone O-methyloxime (1.0 g, 4.11 mmol), as an approximate 96:4 mixute of E and Z oxime isomers, in anhydrous tetrahydrofuran (30 mL) containing trifluoroacetic acid (0.4 mL, 5.14 mmol) was hydrogenated at 1 atm (98,000 Pa) over 10% Pd on C catalyst (200 mg) to cessation of hydrogen uptake (~5 hours, 198 mL hydrogen absorbed). The catalyst was filtered (Celite), washed with tetrahydrofuran (20 mL) and the combined filtrate and wash was added dropwise during 20 minutes to a cold (0°–5° C.), well-stirred suspension of lithium aluminum hydride (1.0 g, 26.31 mmol) in anhydrous tetrahydrofuran (30 mL). The cooling bath was removed after the addition was complete and the mixture stirred at room temperature for 20 hours and then refluxed for 1 hour. The mixture was then cooled to 0°–5° C. and, with good stirring, quenched by the sequential, dropwise addition of water (1.0 mL), 1N NaOH (1.0 mL) and water (3.0 mL). This mixture was stirred for 30 min at 0°–5° C. then filtered through Celite. The filter cake was washed with tetrahydrofuran (2×15 mL) and the combined filtrate and wash concentrated, leaving 0.5 g of 5-amino-5-deoxy-1,2-O-isopropylidene-α-D-glucofuranose. The aluminate salts and Celite were collected and suspended in tetrahydrofuran (40 mL). This mixture was heated at reflux for 30 minutes and then filtered and the collected solids washed with tetrahydrofuran (20 mL). Evaporation of the filtrate yielded an additional 0.1 g of product for a combined yield of 0.6 g (66%). This material by $^1$H NMR analysis was a single isomer and was pure enough to be used without further purification. An analytical sample was obtained as colorless needles by recrystallization from isopropanol-hexane (1:5): mp 120°–121° C.; $[\alpha]_D^{25} -16.2°$ (c 0.57, H$_2$O); $^1$H NMR (300 MHz, d$_6$-DMSO) δ 1.22 (s, 3), 1.36(s, 3), 3.01 (m, 1), 3.54 (dd, 1, J=10.5, 3.7 Hz), 3.76 (dd, 1, J=7.8, 2.8 Hz), 4.04 (d, 1, J=2.8 Hz), 4.36 (d, 1, J=3.7 Hz), 5.8 (d, 1, J=3.7 Hz); mass spectrum (CI,CH$_4$) m/z (rel intensity) 220 (MH+, 100), 202 (MH+-H$_2$O, 13) 162 (41), 144 (21), 99 (16).

This material was converted to 1-deoxynojirimycin-1-sulfonic acid and (+)-1-deoxynojirimycin as described in U.S. Pat. No. 4,908,439, Mar. 13, 1990 (P. B. Anzeveno).

Example 5

1-Deoxynojirimycin-1-sulfonic Acid

A well stirred mixture of 5-(t-BOC)amino-5-deoxy-1,2-O-isopropylidene-α-D-glucofuranose (3.19 g, 10.0 mmol) and saturated aqueous sulfur dioxide (25.0 mL) was heated for 72 hours at 35°–40° C. (oil bath), under nitrogen, in a flask fitted with a mineral oil bubbler. Starting material dissolved during the first few hours of reaction; bisulfite product later began to precipitate. The reaction mixture was cooled in ice, methanol (85 mL) added and the mixture again saturated with sulfur dioxide. After standing at 0° C. overnight, the precipitate was collected by filtration, washed with methanol-ethyl ether (1:1) and dried in vacuo to yield 2.3 g (95%) of 1-deoxynojirimycin-1-sulfonic acid as a white powder. An analytical sample was obtained by recrystallization from water-methanol (1:4) as fine, colorless needles: mp 133°–135° C. dec [lit. 135°–137° C.]; mmp with material from natural nojirimycin, 132°–134° C. dec; $^1$H NMR (D$_2$O, TSP as internal standard) δ 3.32 (ddd, 1, J=10.6, 4.3, 3.1 Hz, H-5), 3.60 (dd, 1, J=9.3, 9.2 Hz, H-3), 3.73 (dd, 1, J=10.6, 9.3 Hz, H-4), 3.9–4.0 (m, 3, H-2, 6,6'), 4.22 (d, 1, J=10.6 Hz, H-1); $^{13}$C NMR (d$_6$-DMSO) δ 58.19, 60.80, 67.72, 69.35, 69.51, 75.77; mass spectrum, m/z (rel intensity) 202 (5), 190 (10), 172 (10), 162 (70), 144 (80), 126 (75), 116 (15), 108 (100).

Example 6

(+)-1-Deoxynojirimycin

A mixture of 1-deoxynojirimycin-1-sulfonic acid (2.5 g, 10.25 mmol), barium hydroxide.8H20 (3.3 g, 10.57 mmol), Raney Ni (~2.5 g) and water (30 mL) was hydrogenated for 24 h on a Parr apparatus at 50 psi. The solids were filtered and washed with water (20 mL). The combined filtrate was lyophilized. Trituration of the residue with methanol (25 mL) provided crystalline (+)-1-deoxynojirimycin (75%). An analytical sample was obtained by recrystallization from (1:3) as colorless prisms: mp 196°–197° C.; $[\alpha]_D^{20} +43.1°$ (c 1.5, H$_2$O) $^1$H NMR (D$_2$O, TSP as internal standard) δ 2.46 (dd, 1, J=12.2, 10.6 Hz, H-1a), 2.55 (ddd, 1, J=9.5, 6.1, 3.2 Hz, H-5), 3.12 (dd, 1, J=12.2, 5.1 Hz, H-1e), 3.23 (dd, 1, J=9.5, 9.3 Hz, H-4), 3.32 (dd, 1, J=9.0, 8.9 Hz, H-3), 3.49 (ddd, 1, J=10.6, 8.9, 5.1 Hz,H-2), 3.63 (dd, 1, J=11.6, 6.3 Hz, H-6), 3.84 (dd, 1, J=11.6, 3.0 Hz, H-6'); $^{13}$C NMR (D$_2$O, TSP as internal standard) δ 51.47, 63.28, 64.19, 73.68, 74.32, 81.18; mass spectrum, m/z (rel intensity) 164 (M++1, 40), 146 (100), 128 (5).

What is claimed is:

1. A process for converting 1,2-O-isopropylidene-5-oxo-α-D-glucuronolactone hydrate to 1-deoxynojirimycin-1-sulfonic acid which comprises (a) reacting 1,2-O-isopropylidene-5-oxo-α-D-glucuronolactone hydrate with an O-substituted hydroxylamine of the formula A—O-NH$_2$, wherein A is C$_{1-4}$ alkyl, benzyl or trimethylsilyl, to give the corresponding oxime which has the formula

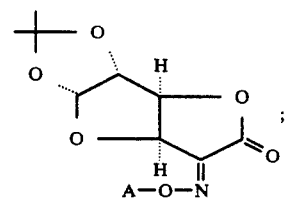

(b) catalytically hydrogenating the oxime using palladium on carbon in the presence of an amine protecting reagent to give 5-(APG)-amino-5-deoxy-1,2-O-isopropylidene-α-D-glucuronolactone wherein APG is an amine protecting group; (c) reducing the 5-(APG)-aminoglucuronolactone with a hydride reducing agent to give 5-amino-5-deoxy-1,2-O-isopropylidene-α-D-glucofuranose or, when APG is t-BOC, 5-(t-BOC)amino-5-deoxy-1,2-O-isopropylidene-α-D-glucofuranose wherein t-BOC is t-butoxycarbonyl; and (d) reacting the glucofuranose with aqueous sulfur dioxide to give the desired 1-deoxynojirimycin-1-sulfonic acid.

2. A process according to claim 1 wherein the t-BOC-anhydride is the amine protecting reagent.

3. A process according to claim 1 wherein the 1-deoxynojirimycin-1-sulfonic acid obtained acid obtained is further hydrogenated over Raney nickel to give (+)-1-deoxynojirimycin.

4. A process according to claim wherein 1 O-benzyl-hydroxylamine is used to prepare the oxime and t-BOC-anhydride is the amine protecting reagent.

5. A process according to claim 4 wherein the aminoglucuronolactone is reduced with lithium aluminum hydride.

6. A process according to claim ,i wherein O-methyl-hydroxylamine is used to prepare the oxime and trifluoroacetic acid is the amine protecting reagent.

7. A process according to claim 6 wherein the aminoglucuronolactone is reduced with lithium aluminum hydride.

8. A process according to claim 5 wherein the 1-deoxynojirimycin-1-sulfonic acid obtained is further hydrogenated over Raney nickel to give (+)-1-deoxynojirimycin.

9. A process according to claim 7 wherein the 1-deoxynojirimycin-1-sulfonic acid obtained is further hydrogenated over Raney nickel to give (+)-1-deoxynojirimycin.

10. A compound selected from 1,2-O-isopropylidene-5-oxo-α-D-glucuronolactone O-methyloxime, 1,2-O-isopropylidene-5-oxo-α-D-glucuronolactone O-benzyloxime and 1,2-O-isopropylidene-5-oxo-α-D-glucuronolactone O-trimethylsilyloxime.

11. A compound according to claim 10 which is 1,2-O-isopropylidene-5-oxo-α-D-glucuronolactone O-methyloxime.

12. A compound according to claim 10 which is 1,2-O-isopropylidene-5-oxo-α-D-glucuronolactone O-benzyloxime.

* * * * *

UNITED STATES PATENT AND TRADEMARK OFFICE
CERTIFICATE OF CORRECTION

PATENT NO. : 5,227,479
DATED : July 13, 1993
INVENTOR(S) : Peter B. Anzeveno, Laura J. Creemer It is certified that error appears in the above-identified patent and that said Letters Patent is hereby corrected as shown below:

In column 6 line 61, the patent reads "3.8 9", and should read -- 3.8g.

In column 10 line 33, Claim 3, the patent reads "acid obtained acid obtained is" and should read --acid obtained is--.

In column 10 line 36, claim 4, the patent reads " claim wherein 1 O-benzyl" and should read --claim 1 wherein O-benzyl--.

In column 10 line 42, claim 6, the patent reads " claim,i wherein" and should read --claim 1--.

Signed and Sealed this

Twenty-eighth Day of June, 1994

Attest:

BRUCE LEHMAN

*Attesting Officer*　　*Commissioner of Patents and Trademarks*